(12) United States Patent
Keller

(10) Patent No.: US 7,803,160 B2
(45) Date of Patent: Sep. 28, 2010

(54) SURGICAL INSTRUMENT FOR GRINDING THE COTYLOID CAVITY

(75) Inventor: Arnold Keller, Kayhude (DE)

(73) Assignee: Waldemar Link GmbH & Co. KG, Hamburg (DE)

(*) Notice: Subject to any disclaimer, the term of this patent is extended or adjusted under 35 U.S.C. 154(b) by 1605 days.

(21) Appl. No.: 10/501,090

(22) PCT Filed: Jan. 10, 2003

(86) PCT No.: PCT/EP03/00191

§ 371 (c)(1),
(2), (4) Date: Nov. 12, 2004

(87) PCT Pub. No.: WO03/057050

PCT Pub. Date: Jul. 17, 2003

(65) Prior Publication Data

US 2005/0049601 A1  Mar. 3, 2005

(30) Foreign Application Priority Data

Jan. 11, 2002 (EP) .................. PCT/EP02/00223
May 15, 2002 (DE) .................. 102 21 614

(51) Int. Cl.
*A61B 17/00* (2006.01)
(52) U.S. Cl. ...................................................... 606/81
(58) Field of Classification Search ............... 606/79, 606/80–81, 178–180; 30/351–353, 356; 623/20.28, 20.29; 408/199
See application file for complete search history.

(56) References Cited

U.S. PATENT DOCUMENTS

| 2,785,673 | A | | 3/1957 | Anderson | |
|---|---|---|---|---|---|
| 3,702,611 | A | * | 11/1972 | Fishbein | 606/81 |
| 4,808,185 | A | * | 2/1989 | Penenberg et al. | 623/20.29 |
| 5,030,219 | A | * | 7/1991 | Matsen et al. | 606/53 |
| 5,176,711 | A | | 1/1993 | Grimes | |
| 5,219,174 | A | * | 6/1993 | Zurbrugg et al. | 279/82 |
| 5,474,560 | A | * | 12/1995 | Rohr, Jr. | 606/91 |
| 5,919,195 | A | * | 7/1999 | Wilson et al. | 606/80 |
| 6,364,910 | B1 | * | 4/2002 | Shultz et al. | 623/19.13 |
| 7,559,928 | B2 | * | 7/2009 | Johnson et al. | 606/81 |
| 2003/0229352 | A1 | * | 12/2003 | Penenberg | 606/81 |
| 2003/0236523 | A1 | * | 12/2003 | Johnson et al. | 606/81 |

FOREIGN PATENT DOCUMENTS

WO  WO-01/91648 A1  12/2001
WO  WO-02/102254    12/2002

OTHER PUBLICATIONS

International Search Report mailed Mar. 27, 2003 directed to corresponding international application No. PCT/EP03/00191; (2 pages).

* cited by examiner

*Primary Examiner*—Thomas C Barrett
*Assistant Examiner*—Nicholas Woodall
(74) *Attorney, Agent, or Firm*—Morrison & Foerster LLP

(57) ABSTRACT

A surgical instrument for grinding the cotyloid cavity includes an instrument head and a drive shaft. In order to offer easier access during a minimally invasive operation, the drive shaft, which can include an optionally provided shank, is located at an angle with respect to the rotation axis of the instrument head. In order to facilitate the alignment of the instrument head and the exertion of the advancing force, a handle can be provided that is located in the direction of the rotational axis of the instrument head but is connected to the instrument head or to the shank at a location outside of the rotational axis.

18 Claims, 3 Drawing Sheets

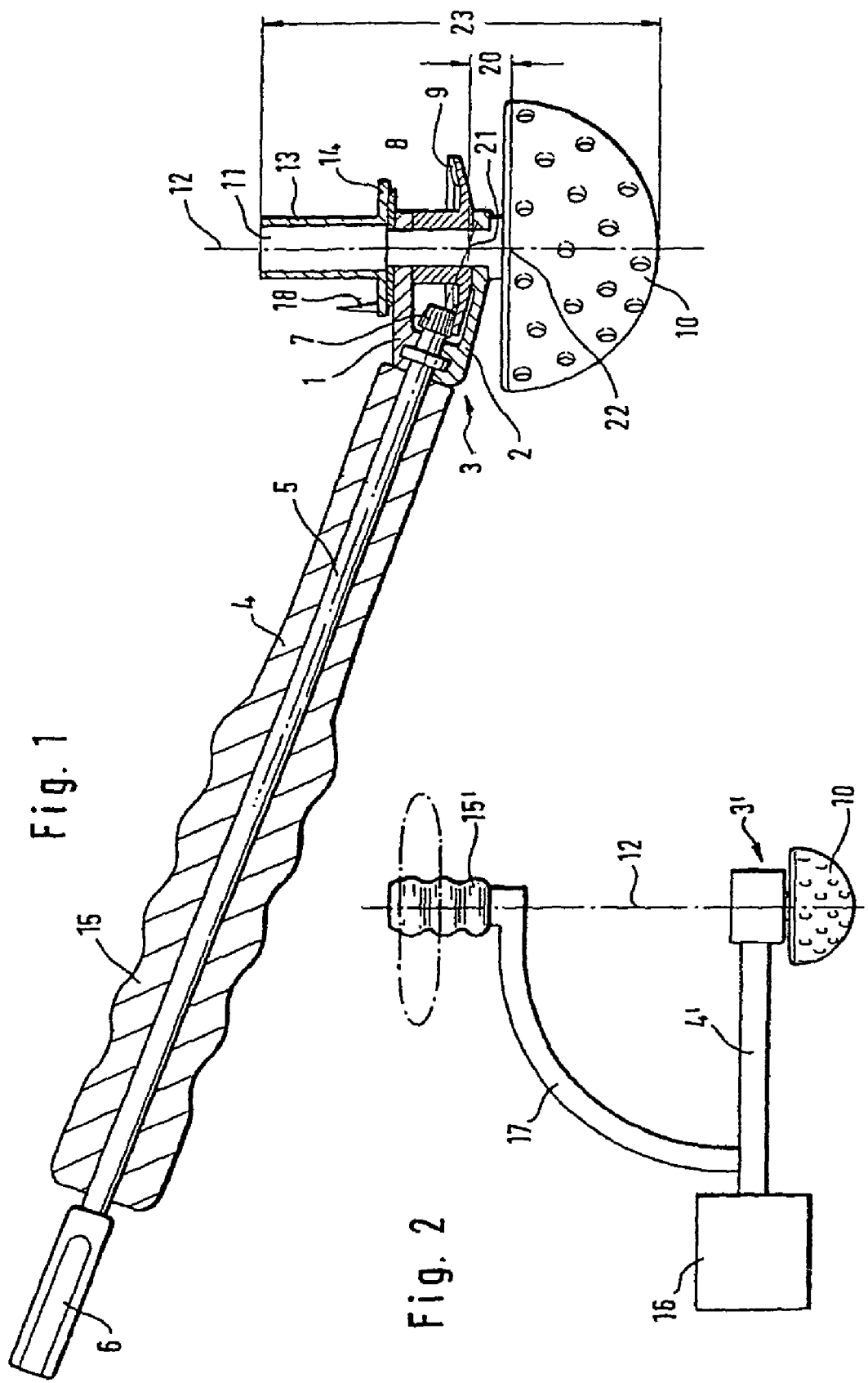

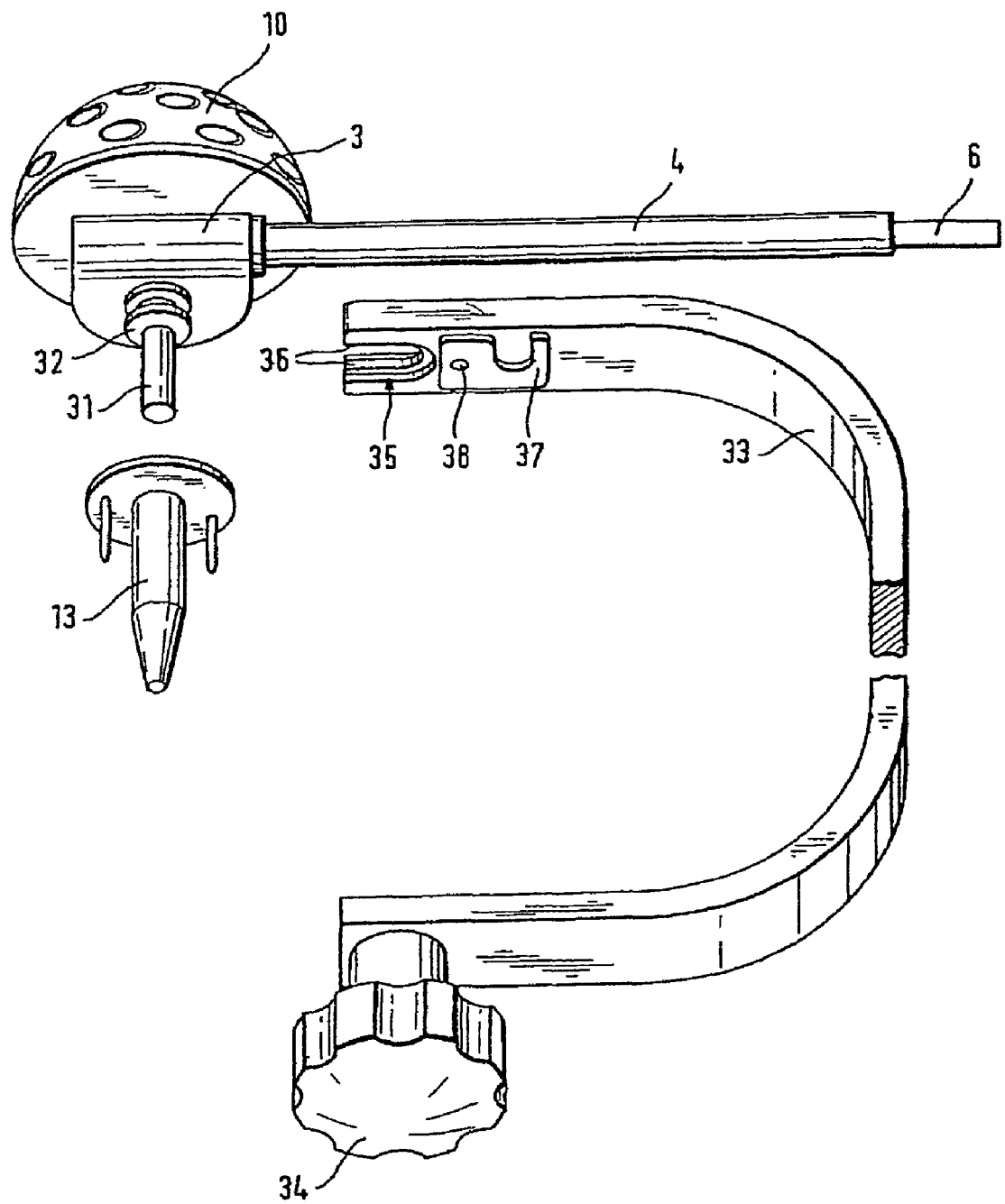

SURGICAL INSTRUMENT FOR GRINDING THE COTYLOID CAVITY

REFERENCE TO RELATED APPLICATIONS

This is a national stage application under 35 USC 371 of International Application No. PCT/EP03/00191, filed Jan. 10, 2003, which claims priority under 35 USC 119 from prior International Application No. PCT/EP02/00223, filed Jan. 11, 2002, and German patent application No. 10221614, filed May 15, 2002.

FIELD AND BACKGROUND OF THE INVENTION

To insert a prosthetic socket into the natural acetabulum, the latter has to be ground out. To do so, it has hitherto been necessary to have an open access in the direction of the acetabulum axis in order to be able to apply a grinding instrument with a shank extending in the grinder axis. This applies even in minimally invasive operating techniques (WO 01/91648, U.S. Pat. No. 2,785,673) when a corresponding bore is created through the proximal part of the femur. This is complicated and weakens the femur. For cases where accessibility is poor, grinding instruments are known (U.S. Pat. Nos. 5,176,711; 4,808,185; 6,364,910, not published) in which the drive shaft is located at an angle with respect to the rotation axis of the instrument head. This makes it difficult to exactly align the grinding instrument with the acetabulum axis and to exert the axial machining force. This applies in particular to minimally invasive access when the operating field is difficult to see or cannot be seen.

SUMMARY OF THE INVENTION

According to the invention, the solution to this difficulty is achieved by a surgical instrument having the features of the invention as broadly disclosed hereinafter.

The instrument has an instrument head equipped with the grinder. The instrument head is connected to a holder by means of which it is held in the desired working position. For driving the grinder, a drive shaft is provided which connects it to a drive device and is located at an angle with respect to the rotation axis of the instrument head. This makes it possible to bring the instrument toward the acetabulum from a direction which does not coincide with the direction in which the acetabulum opens. It is thus suitable for a minimally invasive access to the acetabulum, for example for an anterolateral or posterolateral approach.

According to the invention, a support part is provided which acts on the instrument head in the direction of the rotation axis and makes it possible to apply a machining force in this direction and/or to align the instrument. This support part can be formed by a handle which is connected to the instrument head via a bow located outside of the rotation axis of the instrument head. The bow can also be connected to a pin belonging to the holder of the instrument. The bow allows the instrument head to be brought toward the acetabulum from the side, through what can be a narrow surgical opening, and then to exert an advancing force still in the direction of the working axis. In this way, the operating surgeon also obtains an exact idea of how the operating axis of the instrument lies, which makes it easier for him to align the instrument.

In another embodiment of the invention, the instrument head can also be supported on the femur which, particularly in minimally invasive operating techniques, is sufficiently connected to the hip bone by ligaments and muscles and is therefore able to take up the machining forces. Moreover, according to the invention, the femoral neck can be used for aligning the instrument. This is based on the concept that the direction of the femoral neck in many cases coincides with the desired direction of the grinder. At any rate, this is true if the ligament apparatus is sufficiently retained and the operating surgeon takes care that the leg is in a natural position relative to the acetabulum. For this support on the femur, the holder of the instrument head can have a femur attachment part arranged on that side of the instrument head facing away from the grinder. Depending on the desired purposes, this femur attachment part can be designed with a supporting function only, or with a direction-defining function only, or with both. Further details of this are discussed below.

The holder of the instrument head expediently comprises a shank which, like the drive shaft, is located at an angle with respect to the rotation axis of the instrument head. The angle of the shank or drive shaft with respect to the rotation axis of the instrument head is expediently between 90 and 135°, measured on the side directed toward the grinder. As in the known instruments mentioned, this angle can be invariable. However, it can also be adjustable and if appropriate fixed in a desired position or be freely variable so that the physician can optimally adapt the direction of the handle to the particular circumstances during grinding. The drive shaft can be connected to the shank. However, this is not absolutely necessary. It is preferably flexible if no shank is provided or if this is separate from the drive shaft.

In general, the shank is connected fixedly to the instrument head. However, it may sometimes be advantageous if it is easily detachable, and, from case to case, can be connected to the instrument head and released from the latter during surgery. It is then possible to provide differently designed or oriented shanks in order to satisfy different aims of the operating surgeon and different anatomical conditions. This is true in particular when the bow mentioned above is connected to the shank. The shank is not connected to the drive shaft in the detachable design.

If the femur is used to support the instrument head and/or to determine its direction, this can be done using an attachment part which encloses the femoral neck on the outside along a certain length. In another, preferred embodiment of the invention, the attachment part is formed by a journal which extends in the direction of the rotation axis of the grinder and cooperates with a bore that the operating surgeon has made beforehand from the resection surface into the femoral neck. This journal can be connected fixedly to a housing part of the grinder. It can also be formed by a continuation of the grinder shaft and turn with the grinder. In this case, it is expedient if a bushing is provided which can be fitted into the bore in the femoral neck and receives the journal. The femur attachment part can also be provided with means securing the instrument head against turning.

The femur attachment part can form the only holder for the instrument head. However, it is often expedient to additionally provide the aforementioned shank to ensure that the alignment of the instrument and the advancing movement can be controlled and influenced from outside. In this case, the abovementioned detachable design may be expedient. It may further be expedient to design the femur attachment part and the shank in such a way that they can be used alternately. For example, the journal facing the femur on the instrument head can be used alternately for connection to the shank instead of to the femur. If so desired, the connection between the instrument head and the shank or femur can be of such design that the grinding torque is taken up via the shank or femur.

In the embodiment in which the femur is used as a bearing for generating the advancing force, said advancing force can be generated or increased by the femur attachment part comprising a means for support on the femur and by an extension mechanism being arranged between this support means and the instrument head. This extension mechanism presses the instrument head away from the support means when a corresponding advancing force is exerted on it. For this purpose, it can be connected fixedly or releasably to an advancer rod. The latter should be located at an angle with respect to the rotation axis of the instrument head, like the drive shaft and/or the shank, and specifically to the same side. The extension mechanism forms a gear in its most general sense, which converts the movement set by the advancer rod into an extension of the distance between the instrument head and the support means. A wide variety of gear configurations are readily available to the engineer for this purpose. For example, a lever mechanism can be chosen which converts a pivoting movement of the advancer rod, about a pivot axis lying transverse to the rotation axis of the instrument head, into an extension movement of the extension mechanism. The extension mechanism with the advancer rod can in this case be designed as spreader forceps; in this case the advancer rod is formed by a pair of forceps levers. The extension mechanism can also be formed by a rotary gear; in this case the advancer rod is turned in order, for example, to act, via a pinion provided at its end, on a toothed rack which effects the extension of the mechanism.

So that the instrument head can be introduced from the side through a narrow surgical opening, its size should be kept as small as possible in the direction of the grinder axis. A measure of this size is the distance between the intersection point of the rotation axis of the instrument head with the axis of the shank or drive shaft, on the one hand, and the center point of the grinder, on the other hand. This distance should be as small as possible. It should not be greater than the grinder diameter and preferably not greater than half the grinder diameter. The external size of the instrument head, measured in the direction of the grinder axis, is expediently not greater than 8 cm, preferably not greater than 6 cm.

BRIEF DESCRIPTION OF THE DRAWINGS

The invention is explained in more detail below with reference to the drawing which shows advantageous illustrative embodiments.

FIG. 1 shows a longitudinal section through the instrument,

FIG. 2 shows a diagrammatic view of an alternative embodiment of the instrument, FIG. 5 shows a fifth embodiment.

DETAILED DESCRIPTION OF THE INVENTION

Figure 3:
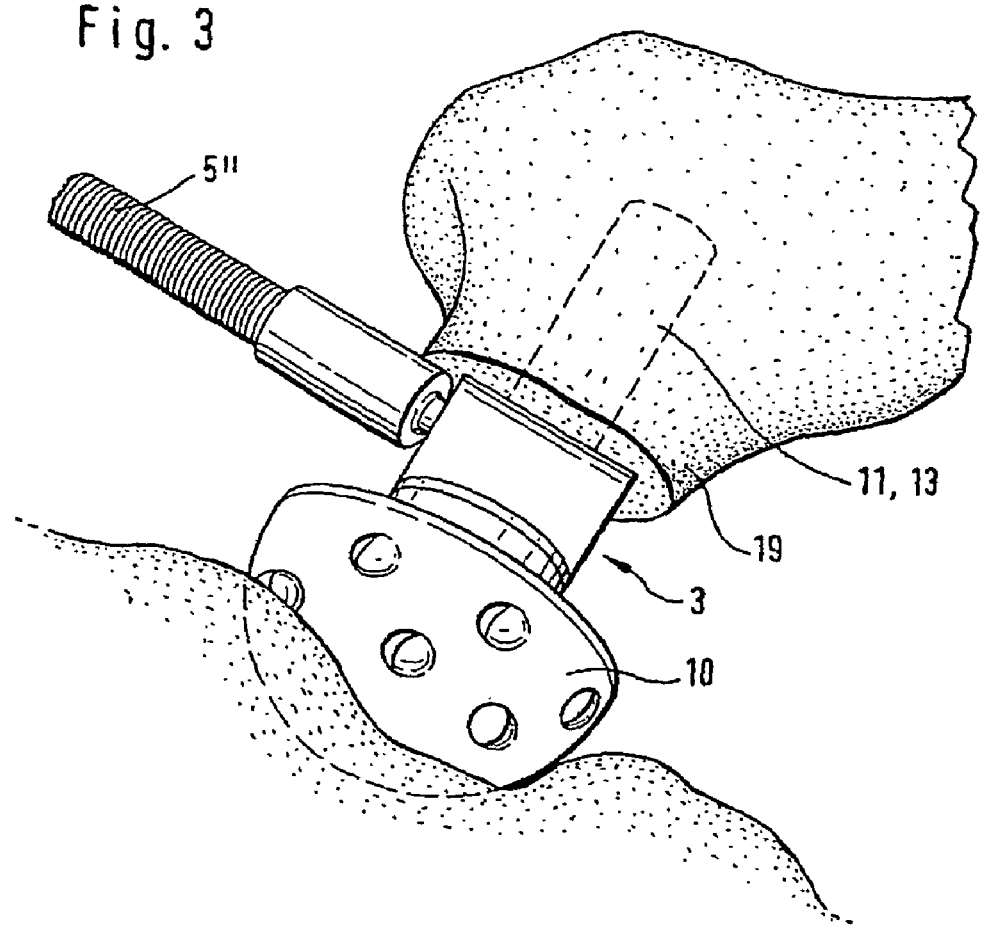
FIG. 3 shows a third embodiment of the equipment in use.

The housing parts 1, 2 of the instrument head 3 shown in FIG. 1 are connected fixedly to a shank 4 which forms a handle 15 and contains a drive shaft 5 whose free end 6 can be connected in a known manner to a drive motor or to a grip for manual operation. Inside the housing 1, 2, the drive shaft 5 carries a toothed pinion 7.

Also in the housing 1, 2 of the instrument head 3, a grinder shaft 8 is also mounted so as to rotate transverse to the drive shaft 5. The angle between the two shafts is expediently between 90 and 135° (110° in the case shown). The grinder shaft carries a bevel gear 9 whose teeth engage with those of the pinion 7. The grinder shaft 8 can in this way be driven in rotation by the drive shaft 5. It will be appreciated that this is just one example of the drive connection between the two shafts. Other gear types can be used, for example a worm gear. The gear itself, or a cardan part connected to it, can be configured with angle tolerance in order to permit adjustment of the angle between the shafts 5 and 8. A fixing means can be provided which allows the instrument to be locked in the chosen angle setting. Instead of this, it is also possible to provide free angle movement.

A semispherical grinder tool 10, known per se, and referred to in this description simply as a grinder, is fitted onto the end of the grinder shaft 8 in a manner known per se and so as to be exchangeable. To keep the size of the instrument head to a minimum, the grinder is located close up to the housing 1, 2 of the instrument head.

The distance of the center point 22 of the grinder or of the center point of its rear face from the intersection point 21 of the axes of the shafts 5 and 8 is smaller than the radius of the grinder, preferably smaller than a quarter of the grinder diameter. If the grinder is not semispherical in shape, said diameter is replaced by the greatest diameter.

Extending from the side of the instrument head 3 facing away from the grinder 10, there is a journal 11 which is connected fixedly, if appropriate in one piece, to the grinder shaft 8 and has a common rotation axis 12 with the latter. A sleeve 13 with terminal flange 14 is fitted onto the journal 11 with a sliding fit. On its side facing toward the bone, the flange has teeth or needles 18 which penetrate into the bone in order to prohibit rotation of the sleeve 13.

The instrument is used in the following way. After the head of the hip has been removed, a blind hole is formed in the femoral neck, starting from its resection surface and on the same axis, and the sleeve 13 is inserted into this blind hole. The instrument is introduced in such a way that the journal 11 is fitted into the sleeve 13 sitting in the bore in the femur. The leg is positioned normally so that the femoral neck points to the acetabulum and the grinder lies in place of the natural head of the hip in or on the acetabulum. The grinder 10 is pressed into the acetabulum by the ligaments holding the proximal femur and is at the same time aligned naturally. The acetabulum can now be ground out completely, with or without slight orientation assistance from the operating surgeon. Thereafter, the operation is continued in the known manner.

While the illustrative embodiment according to FIG. 1 makes do with a handle shank protruding transversely from the instrument head 3, an instrument is indicated diagrammatically in FIG. 2 whose handle 15' is arranged approximately in the axis 12 of the grinder 10. The shank 4' of the instrument protrudes approximately perpendicularly from the instrument head 3' and carries a drive motor 16 at its end. The end of the shank 4' is connected rigidly to the handle 15' by means of a bow 17. The position of the handle provides the operating surgeon with a precise indicator of the position of the grinder axis 12 and allows him not only to align the grinder in the desired axis direction but also to control the force with which the grinder is pressed into the acetabulum. The handle can be designed flat in the dot-and-dash line to make it easier to orient the force with the hand or the body of the operating surgeon.

The instrument according to FIG. 3 differs from the one shown in FIG. 1 in that it does not have a shank, and the drive shaft 5" is designed as a flexible shaft. As has been explained with reference to FIG. 1, the alignment of the instrument is effected by the sleeve 13 inserted into the bone 19 and by the journal 11 located therein. The advancing force needed for grinding is also transmitted from the bone 19 to the instrument. By virtue of the flexibility of the drive shaft 5', the alignment of the instrument defined by the femur is not adversely affected by inadvertent movements of the operating surgeon. However, the shaft 2' is stiff enough to be able to transmit the grinding torque. A rotationally fixed connection can also be provided between the instrument head 3 and the flange of the sleeve 13, the flange in turn being connected in a rotationally fixed manner to the bone by teeth or needles 18 (FIG. 1) in order to bear on the latter in respect of the grinding torque.

Figure 4:
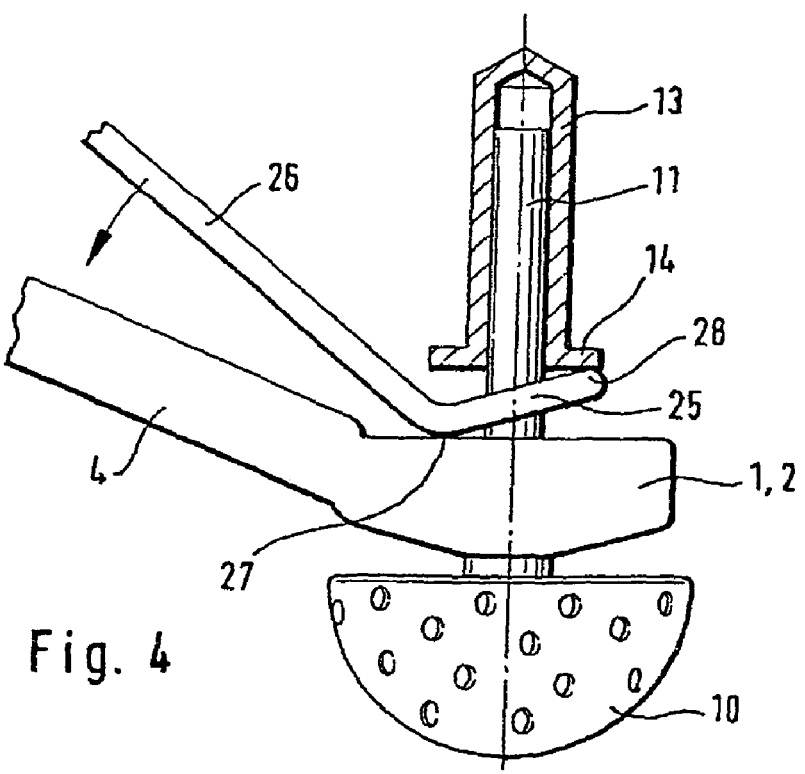
FIG. 4 shows a fourth embodiment.

FIG. 4 shows a variant of the instrument, for whose description reference may be made to FIG. 1. The end 25 of a lever 26 is interposed between the housing 1, 2 and the flange 14. This end is designed like a fork so that, if desired, it can be pushed in at a later stage between the housing 1, 2 and the flange 14. It is angled slightly with respect to the long end 26 of the lever. It is first pushed in parallel between the rear face of the housing 1, 2 and the flange 14. The long end 26 of the lever is then located at a certain angle distance from the shank 4. If an advancing force is to be generated in order to press the grinder 10 into the acetabulum, the long end 26 of the lever is pressed toward the shank 4 in the direction of the arrow. The operating surgeon can execute this movement easily in the manner of actuating a forceps. In doing so, the bend point 27 of the lever bears on the rear face of the housing 1, 2 and forms the pivot point for its subsequent pivoting movement. The tip 28 bears on the flange 14 and presses it away from the housing 1, 2 as the pivoting movement continues. The lever end 25 thus forms an extension mechanism together with the rear face of the housing 1, 2 and the flange 14. The long end 26 of the lever forms an advancer rod, upon whose movement the extension mechanism is extended in order to increase the distance of the grinder 10 from the bone 19 on which the flange 14 of the sleeve 13 bears, and thus to press the grinder 11 into the acetabulum.

In the fifth embodiment according to FIG. 5, a grinder 10 is connected to the instrument head 3 in the manner explained above. A shank 4 is connected to the instrument head 3 at right angles to the grinder axis, said shank 4 containing a drive shaft to whose free end 6 a drive motor can be coupled. A journal 31 is rigidly connected to the instrument head 3. It can be inserted into the bore of a sleeve 13 which for its part is fitted into the femoral neck remaining after resection of the head of the hip, as has been described above. The journal 31 then serves to orient the instrument head 3 and the grinder 10 in the direction of the neck of the femur. In this way too, the necessary press-on force can be transmitted to the grinder 10.

In order to be able to transmit additional force to the instrument head 3 and if appropriate also to be able to align the instrument, a bow 33 with handle 34 is provided. The handle lies in the same axis as the rotation axis of the grinder 10 and the axis of the journal 31. The bow is made stiff enough to be able to transmit the press-on force and guiding force from the handle 34 to the instrument head 3. Coupling members 32, 35 matching each other are provided on the instrument head 3 and at the end of the bow 33 remote from the handle, these coupling members 32, 35 preferably being designed in such a way that they can be closed or released quickly and simply, as may be necessary during the operation. For such couplings, a large number of technical possibilities are available. In the example shown, they are configured as follows. On the bow, a coupling fork 35 is provided which has a fork opening delimited by profiled fork flanks 36 on both sides. The coupling element 32 on the instrument head 3 is designed to match the fork opening and has a profiled contour complementing that of the flanks 36. For example, the flanks 36 can have a central rib corresponding to a groove on the coupling element 32. The coupling element 32 is round, so that the coupling fork 35 can be fitted on from any direction. This construction gives the operating surgeon freedom in respect of the direction from which he wishes to fit the bow onto the instrument. If this is not desired, the coupling element 32 can, for example, be designed as a square with parallel profiled sides which fit into the coupling opening of the fork 35, but define a coupling direction with the latter.

To ensure that the coupling fork 35 cannot inadvertently slip from the coupling element 32 on the instrument, a securing hook 37 is provided which is pivotable about an axis 38 so that it can be moved from the release position, shown in FIG. 5, to the securing position in which it closes around the journal 31 when the coupling element 32 is located in the fork opening, and vice versa. The securing hook can be connected to a locking device which prohibits undesired withdrawal from the securing position.

The invention claimed is:

1. A surgical instrument for grinding the cotyloid cavity, comprising an instrument head having a rotation axis and with grinder thereon, a holder for holding the instrument head in a working position, a drive device, a drive shaft which connects the grinder to the drive device and is located at an angle with respect to the rotation axis of the instrument head, and a support part arranged in the direction of the rotation axis and acting on the instrument head, wherein the support part comprises a femur attachment part arranged on a side of the instrument head facing away from the grinder, the femur attachment part determines a grinding direction, and the femur attachment part comprises a journal extending in the direction of the rotation axis of the instrument head.

2. The instrument as claimed in claim 1, wherein the holder comprises a shank located at an angle with respect to the rotation axis of the instrument head.

3. The instrument as claimed in claim 2, wherein the drive shaft is arranged in or on the shank.

4. The instrument as claimed in one of claims 1 through 3, wherein the journal is formed by a grinder shaft.

5. The instrument as claimed in claim 4, further comprising a bushing for the journal formed by the grinder shaft which can be inserted into a bore in the femur.

6. The instrument as claimed in claim 5, wherein the angle between the rotation axis of the instrument head and the drive shaft or the shank is adjustable.

7. The instrument as claimed in claim 5, further comprising a separate shank detachably connected to the instrument head.

8. The instrument as claimed in claim 5, further comprising a grinder advancer device for advancing the instrument head with support on the femur.

9. The instrument as claimed in claim 8, wherein the femur attachment part comprises a support on the femur, and wherein the instrument further comprises an extension mechanism arranged between the support and the instrument head.

10. The instrument as claimed in claim 5, wherein the instrument has an outer dimension, measured in the direction of the grinder axis without including parts optionally to be accommodated in the femur and including the grinder, of not greater than 8 cm.

11. The instrument as claimed in claim 4, wherein the angle between the rotation axis of the instrument head and the drive shaft or the shank is adjustable.

12. The instrument as claimed in one of claims 1 through 3, wherein the angle between the rotation axis of the instrument head and the drive shaft or the shank is adjustable.

13. The instrument as claimed in one of claims 1 through 3, further comprising a separate shank detachably connected to the instrument head.

14. The instrument as claimed in one of claims 1 through 3, further comprising a grinder advancer device for advancing the instrument head with support on the femur.

15. The instrument as claimed in claim 14, wherein the femur attachment part comprises a support on the femur, and wherein the instrument further comprises an extension mechanism arranged between the support and the instrument head.

16. The instrument as claimed in one of claims 1 through 3, wherein the distance between the intersection point of the rotation axis of the instrument head and the axis of the shank or drive shaft, on the one hand, and the center point of the grinder, on the other hand, is not greater than the grinder diameter.

17. The instrument as claimed in claim 16, wherein the distance is not greater than half the grinder diameter.

18. The instrument as claimed in one of claims 1 through 3, wherein the instrument has an outer dimension, measured in the direction of the grinder axis without including parts optionally to be accommodated in the femur and including the grinder, of not greater than 8 cm.

* * * * *